United States Patent [19]

Gammans et al.

[11] Patent Number: 4,613,600
[45] Date of Patent: Sep. 23, 1986

[54] ANTIDEPRESSANT 1,2,4-TRIAZOLONE COMPOUNDS

[75] Inventors: Richard E. Gammans; David W. Smith, both of Evansville; Joseph P. Yevich, Newburgh, all of Ind.

[73] Assignee: Mead Johnson & Company, Evansville, Ind.

[21] Appl. No.: 538,027

[22] Filed: Sep. 30, 1983

[51] Int. Cl.$^4$ .................. C07D 249/00; A61K 31/41
[52] U.S. Cl. ...................................... 514/252; 544/366
[58] Field of Search ...................... 544/366; 424/250

[56] References Cited

U.S. PATENT DOCUMENTS 3,381,009  4/1968  Palazzo et al. ................. 424/250
3,857,845  12/1974  Palazzo ............................ 544/366
4,338,317  7/1982  Temple, Jr. et al. ............ 544/366

OTHER PUBLICATIONS

La Selva, et al., *Riv. Neuropsichiat. Sci. Affini.*, 25/2, 57–68 (1979).
Silvestrini, et al., *International Journal of Neuropharmacology*, 7, 587–599 (1968).
Fabre, et al., *Current Therapeutic Research*, 25, 827–834 (1979).
Temple, Jr., et al., U.S. Ser. No. 06/509,266 filed 6/29/83.

*Primary Examiner*—George F. Lesmes
*Assistant Examiner*—S. A. Gibson
*Attorney, Agent, or Firm*—Richard P. Ryan; Robert H. Uloth

[57] ABSTRACT

2-[3-[4-(3-Halophenyl)-1-piperazinyl]propyl]-5-(1-hydroxyethyl)-2,4-dihydro-[4-phenoxyalkyl-3H-1,2,4-triazol-3-ones and closely related compounds are psychotropic agents having promise as antidepressants by virtue of their receptor site binding affinity profiles and animal pharmacology.

13 Claims, No Drawings

ANTIDEPRESSANT 1,2,4-TRIAZOLONE COMPOUNDS

BACKGROUND OF THE INVENTION

The present invention relates to 1,2,4-triazole heterocyclic carbon compounds and to their preparation and use. More particularly, the invention relates to 2-[3-[4-(3-halophenyl)-1-piperazinyl]propyl]-5-(1-hydroxyethyl)-2,4-dihydro-4-phenoxyalkyl-3H-1,2,4-triazol-3-ones and their therapeutic use in treating depression.

The tranquilizing compound known as etoperidone; chemically, 2-[3-[4-(3-chlorophenyl)-1-piperazinyl]-propyl]-4,5-diethyl-2H-1,2,4-triazol-3(4H)-one, was disclosed by Palazzo in U.S. 3,857,845 which issued 12/1974. Etoperidone is depicted structurally below as (1)

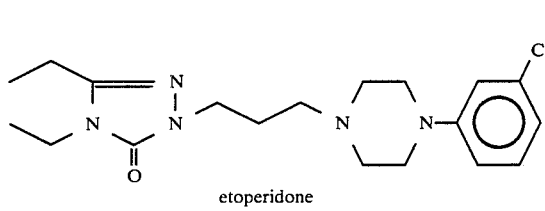

etoperidone and has been studied clinically; cf: La Selva, et al., *Riv. Neuropsichiat. Sci. Affini*, 25/2, 57–68, 1979 (in Italian: English summary).

Etoperidone is in turn related to a series of 1,2,4-triazolo[4,3-a]pyridines of general formula (2) disclosed by Palazzo, et al., in U.S. Pat. No. 3,381,009 to exhibit tranquilizing action.

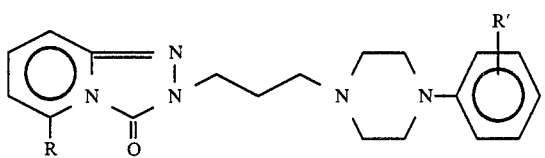

In the above structure R is hydrogen or methyl and R' is hydrogen, lower ($C_{1-4}$) alkyl, lower alkoxy, or halogen. Pharmacological properties of one compound of this series in particular, trazodone; chemically, 2-[3-[4-(3-chlorophenyl)-1-piperazinyl]propyl]-1,2,4-triazolo[4,3-a]pyridin-3(2H)-one, have been described in more detail by Silvestrini, et al., *International Journal of Neuropharmacology*, 7, 587–599 (1968). Trazodone has been studied extensively in man and is currently marketed as an antidepressant agent which is equivalent in effectiveness to imipramine but having fewer side effects (Fabre, et al., *Current Therapeutic Research*, 25, 827–834 (1979)).

Also related is a series of compounds having structure (3) as disclosed by Temple, Jr., et al. in U.S. Pat. No. 4,338,317 which issued July 6, 1982.

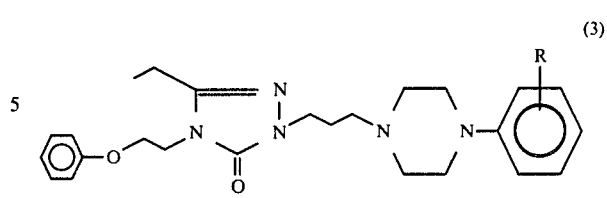

In the above structure (3), R is halogen. The most preferred embodiment of this series is the compound of Formula (3) wherein R is meta-chloro; this compound being commonly known as nefazodone and is also referred to as MJ 13754. Currently, nefazodone is undergoing clinical study as an antidepressant agent under investigational new drug status.

It is of interest in regard to the compounds of the instant invention that a major metabolic pathway for both etoperidone and nefazodone involves alpha-carbon hydroxylation of the ethyl group located in the 5-position of the triazolone ring. This has been confirmed, for example, by comparison of metabolic isolates of nefazodone with the synthetically available corresponding 5-hydroxyethyl analog of the instant invention.

Attention is also called to pending application Ser. No. 06/509,266 which is a continuation-in-part of the U.S. Pat. No. 4,338,317 subject matter (nefazodone) and discloses a series of compounds including those depicted by structure (4)

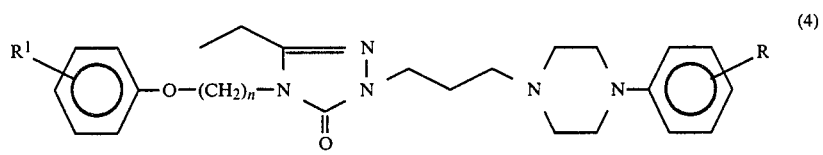

In the above structure, n is 2–4, R remains halogen, and $R^1$ is hydrogen, halogen, alkoxy, or trifluoromethyl.

SUMMARY OF THE INVENTION AND DESCRIPTION OF PREFERRED EMBODIMENTS

The present invention includes the compounds of Formula I and the acid addition salts of these substances.

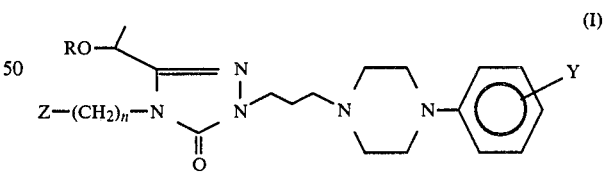

In the foregoing structural formula the symbol R designates hydrogen; lower ($C_1$–$C_4$) alkyl; lower acyl; phenyl-lower-alkyl, such as benzyl; and phenyl-lower-acyl, such as phenacyl; Y is halogen, preferably chloro, and trifluoromethyl; Z is hydrogen and

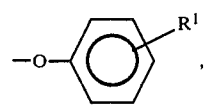

with $R^1$ being hydrogen, halogen, $C_{1-4}$ alkoxy, and trifluoromethyl; and n is 2–4. The compounds of the present invention are psychotropic agents displaying selective central nervous system effects which are associated with useful antidepressant activity. The most preferred compound of this series has the structure (Ia) and is also known as MJ 14808.

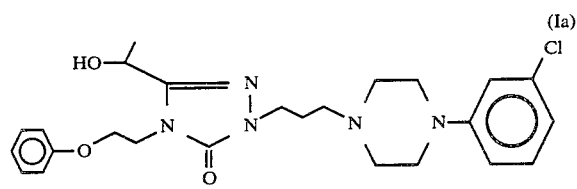
(Ia)

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of structure I with an inorganic or organic acid, preferably by contact in solution, or by any of the standard methods detailed in the literature and available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, tannic acid, and the like; useful inorganic acid are hydrohalic acids such as HCl, HBr, HI; sulfuric acid, phosphoric acid; and the like.

Inventors contemplate that equivalents of their invention would be embodied by inclusion of the structural modifications disclosed in the related above-cited Temple, et al. patent and patent application. For example, one class of equivalents would be those compounds in which the aromatic ring on the 4- position of piperazine was replaced with a hetero aryl system such as pyridine, a diazine, and so forth.

Since the alpha-carbon atom of the 5-ethyl group is asymetric, it is also to be understood that the compounds of the present invention include all of the optical isomer forms, that is, mixtures of enantiomers, e.g., racemic modifications as well as the individual enantiomers. These individual enantiomers are commonly designated according to the optical rotation they affect, by (+) and (−), (1) and (d), or combinations of these symbols. The individual optical isomers can generally be obtained by one of four basic methods. These are: (1) fractional recrystallization of chiral acid salt derivatives; (2) derivatization with a chiral organic reagent, resolution and regeneration of the original compound in optically active form; (3) synthesis of the single optical isomer using chiral intermediates; and (4) column chromatography utilizing chiral stationary phases. Applications of these various methods are well known to practitioners in the art.

The Formula I compounds are useful pharmacological agents with psychotropic properties. In this regard, they exhibit selective central nervous system effects associated with antidepressant activity according to conventional in vivo test systems such as those listed below.

| Behavioral Test | Reference |
|---|---|
| Suppression of Conditioned Avoidance Response (CAR) | Albert, et al., Pharmacologist, 4, 152 (1962). |
| Prevention of Reserpine Ptosis in Mice (antidepressant test) | Niemegeers, Industrial Pharmacology, Vol 2 - Antidepressants, edit. by S. Fielding and H. Lal, pp. 73-98, Futura, New York, N.Y. (1975). |

In these tests, MJ 14808 suppressed CAR in the rat and prevented, but did not reverse, reserpine ptosis in the mouse. Such activity is characteristic of most clinically useful antidepressant agents.

As further indication of the psychotropic activity and specificity of the instant compounds, state of the art in vitro central nervous system receptor binding methodology can be employed. Certain compounds (commonly referred to as ligands) have been identified which preferentially bind to specific high affinity sites in brain tissue dealing with psychotropic activity or potential for side effects. Inhibition of radiolabeled ligand binding to such specific high affinity sites is considered a measure of a compound's ability to affect corresponding central nervous system function or cause side effects in vivo.

The following tests, as well as others, can be employed in developing a profile of the psychotropic activity of the instant compounds.

| Receptor Binding Assay | Reference |
|---|---|
| Dopamine | Burt, et al., Molecular Pharmacology, 12, 800 (1976); Science, 196, 326 (1977); Creese, et al., Science, 192, 481 (1976). |
| Cholinergic | Yamamura, et al., Proceedings National Academy of Science, USA 71, 1725 (1974). |
| Alpha-receptor | Crews, et al., Science, 202:322 (1978); Rosenblatt, et al., Brain Research, 160: 186 (1979); U'Pritchard, et al., Science, 199:197 (1978); U'Pritchard, et al., Molecular Pharmacology, 13:454 (1977). |
| Serotonin Type 2 | Peroutka and Snyder, Molecular Pharmacology, 16:687 (1979). |

According to the foregoing assays, MJ 14808 inhibits serotonin binding and was relatively inactive with respect to dopamine receptor binding, cholinergic receptor binding, and alpha-receptor binding. The latter is particularly significant in that drugs with high affinity for alpha-receptors relative to serotonin type 2 receptors are likely to cause side effects such as sedation and blood pressure lowering. Thus, the instant compounds, selected representatives of which give similar binding and biological test results are considered useful antidepressants.

According to the present invention, the piperazinylalkyl-1,2,4-triazol-3-ones characterized by Formula I are obtained by the following synthetic processes shown below as Scheme 1.

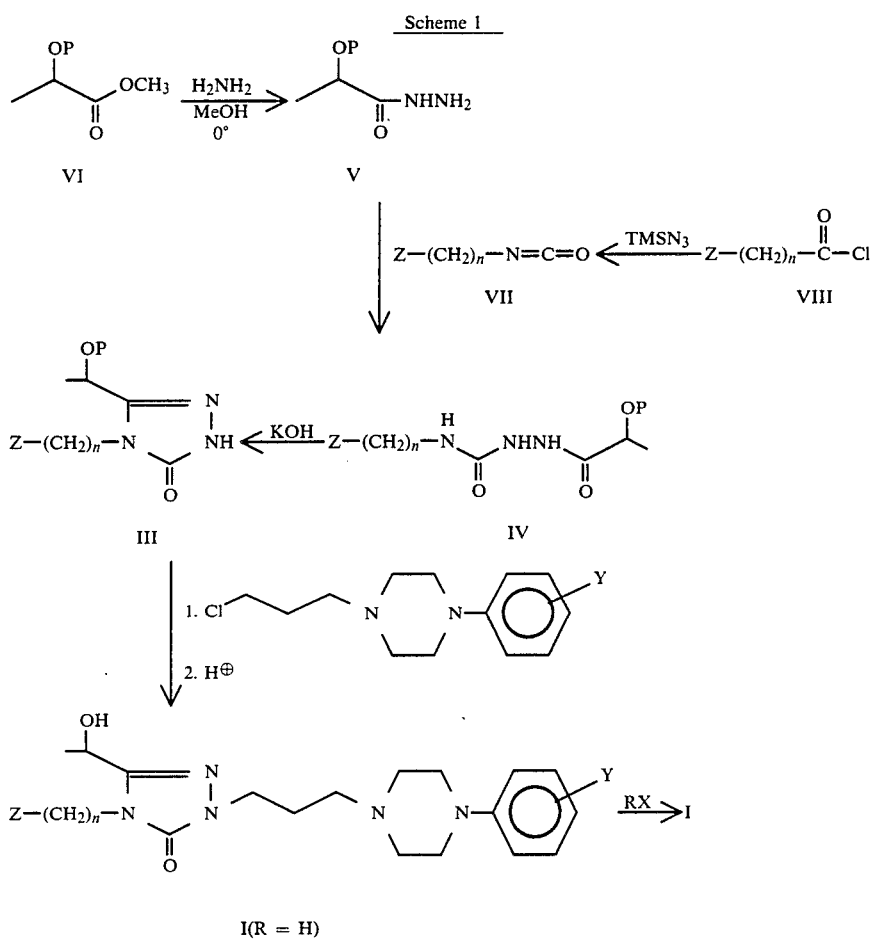

Scheme 1

I(R = H)

In the above scheme, Y, Z and n are as defined above and P represents an acid-labile protecting group; a preferred group being the methoxymethyl moiety. P may also be lower ($C_{1-4}$) alkyl or lower alkylphenyl, for those cases in which the corresponding Formula I ether product is desired. $TMSN_3$ is an abbreviation for trimethylsilyl azide; R is lower ($C_{1-4}$) alkyl, lower alkylphenyl, lower acyl, or lower acylphenyl; and X comprehends halogen, preferably bromine or iodine, or a suitable leaving group such as sulfate, phosphate, tosylate, mesylate, and the like.

The above depicted synthetic process involves reaction of a suitably protected lactic acid ester (VI) with hydrazine in cold methanol to give the hydrazide intermediate (V). A reactive isocyanate (VII) is generated in situ by heating a suitably selected alkanoic acid (VIII) chloride with trimethylsilyl azide. Preparation of the requisite isocyanates may be achieved by use of a procedure similar to that described hereinafter in Example 1(c). Following the in situ generation of (VII), (V) is introduced and the subsequent reaction yields the semicarbazide intermediate product (IV). Cyclization of (IV) to give (III) is accomplished by refluxing in 5% KOH solution. Alkylation of (III) with 1-(3-chloropropyl)-4-(3-chlorophenyl)piperazine (II) followed by dilute acid cleavage of the protecting group provides the appropriate Formula I product. If the Formula I product desired is an ether (where R is lower alkyl or lower alkylphenyl) such a product may be prepared by reacting 2-chloropropionic acid with 2 molar equivalents of the desired alkoxide in a suitable solvent (usually the alcohol from which the alkoxide was derived) followed by esterification and reaction with anhydrous hydrazine to give V with P corresponding to R according to the alkoxide selected. Continuation of the synthetic process outlined as Scheme 1, but without dilute acid cleavage in the final step, provides I, $R^1$=alkyl, phenylalkyl. Alternatively, the secondary alcohol group of (Ia) may be converted into the desired $OR^1$ moieties comprising (I) by O-alkylation or acylation using the appropriate agents well known to a practitioner skilled in the chemical arts.

The starting lactate intermediates (VI) can be conveniently obtained either by heating an appropriate lactate ester with a protecting group reagent such as dimethoxymethane; or by treating a 2-halo propionate with a sodium alkoxide reagent. The reaction intermediate (II) is prepared according to the synthesis disclosed in the Temple, Jr., et al. patent U.S. Pat. No. 4,338,317 which is hereby incorporated by reference.

It is also of interest that MJ 14808 (Ia) was used to confirm the identity of a major metabolite of MJ 13754 by demonstration that the mass spectra and gas chromatographic retention times were the same. In this regard, another aspect of the instant invention comprises 2-[3-[4-(3-chlorophenyl)-1-piperazinyl]propyl]-5-(1-hydroxyethyl)-2,4-dihydro-4-(2-phenoxyethyl)-3H-1,2,4-triazol-3-one (MJ 14808) and 2-[3-[4-(3-chlorophenyl)-1-piperazinyl]propyl]-4-ethyl-5-(1-hydroxyethyl)-2H-1,2,4-triazol-3(4H)-one in purified pharmaceutically acceptable form.

Another aspect of the instant invention provides a method for treating a mammal afflicted with depression which comprises administering systemically to said mammal a therapeutically effective antidepressant amount of a compound of Formula I or a pharmaceutically acceptable acid addition salt thereof. The use and administration of the compounds of the instant invention is considered to be done in the same fashion as for the reference drug trazodone. An effective dose ranges from 0.01 to 40 mg/kg of body weight with a dosage dependent on effects sought, manner of administration, and to some extent with a particular compound selected. A preferred dosage range is 0.5 to 1.5 mg/kg body weight. Systemic administration refers to oral, rectal and parenteral (i.e. intramuscular, intravenous and subcutaneous). Generally, it will be found that when a compound of the present invention is administered orally, or larger quantity of the active agent is required to produce the same effect as a smaller quantity given parenterally. In accordance with good clinical practice, it is preferred to administer the instant compounds at a concentration level that will produce effective antidepressant effects without causing any harmful or untoward side effects.

The compounds of the present invention may be administered for antidepressant purposes either as individual therapeutic agents or as mixtures with other therapeutic agents. Therapeutically, they are generally given as pharmaceutical compositions comprised of an antidepressant amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g sodium lauryl sulfate). Solutions or suspensions of a Formula I compound with conventional pharmaceutical vehicles are employed for parenteral compositions such as an aqueous solution for intravenvous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic process, temperatures are expressed in degrees Celsius and melting points are uncorrected. The nuclear magnetic resonances (NMR) spectral characteristics refer to chemical shifts ($\gamma$) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad (bs), singlet (s), multiplet (m), or doublet (d). Abbreviations employed are DMSO-$d_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

EXAMPLE 1

2-[3-[4-(3-Chlorophenyl)-1-piperazinyl]propyl]-5-(1-hydroxyethyl)-2,4-dihydro-4-(2-phenoxyethyl-3H-1,2,4-triazol-3-one (Ia)

a. Methods of preparation of hydroxy group-protected lactic acid esters (VI) are well known to chemical practitioners. One convenient method involves the use of dimethoxymethane (methal) for preparation of a methoxymethyl ether-protected hydroxy group. For general methodology cf: Yardley and Fletcher, *Synthesis*, 1975, 244. Typically, an equivalent of methyl lactate, 5 equivalents of methal, and a catalytic amount (0.1 g) of p-toluenesulfonic acid are refluxed in methylene chloride for several days and the methanol produced is removed by azeotropic distillation. Following completion of the reaction, a small amount of triethylamine is added and the reaction mixture is washed with brine, the organic phase dried (K$_2$CO$_3$) and concentrated in vacuo to a residue which is distilled to yield crude product (b.p. 95°–105° at 20–30 Torr.). This crude material was used without further purification.

b. The methoxymethyl ether derivative of methyl lactate (6.3 g, prepared above in a.) was added dropwise to a stirred, cold (0°) solution of hydrazine (1.36 g, 1.35 mL) in 10 mL methanol. After completion of the addition, the reaction mixture was placed in a freezer (approximately −10°) for 18 hours. The methanol was then removed under reduced pressure and the residue distilled to give hydrazide product (V) as a clear oil, b.p. 90°–115° at 0.8 Torr.

Anal. Calcd. for C$_5$H$_{12}$N$_2$O$_3$: C, 40.52; H, 8.18; N, 18.91. Found: C, 39.96; H, 8.06; N, 18.57.

Spectroscopy (IR, NMR, and mass spectrum) were all consistent with the assigned structure.

c. A solution of trimethylsilyl azide (2.05 g, 2.36 mL, 1.1 equivalent) in 1 mL toluene was added dropwise to a hot (approximately 100°) solution of 3-phenoxypropionyl chloride in 2 mL toluene. This reaction mixture was heated at 95°–100° for 3½ hours after addition of the azide reagent. The toluene and by-product trimethylsilyl chloride were removed by distillation. The residual isocyanate intermediate was added to a cold (0°) solution of (V, 2.4 g, 16.2 mmole, 1.0 equivalent) in approximately 5 mL methylene chloride. This reaction mixture was stored in a freezer for 16 hours during which time the semicarbazide product (IV) crystallized from solution. Recrystallization from 1,2-dichloroethane gave white solid, m.p. 88°–90°.

Anal. Calcd. for C$_{14}$H$_{21}$N$_3$O$_5$: C, 54.00; H, 6.81; N, 31.50. Found: C, 53.66; H, 6.79; N, 31.10.

Spectroscopy (IR, NMR, and mass spectrum) was consistent with the assigned structure.

d. The semicarbazide (IV) is cyclized to (III) by refluxing in 5% KOH solution. This semicarbazide (IV), 3.1 g) was dissolved in approximately 35 mL 5% KOH solution. The reaction mixture was refluxed under nitrogen for 5 hours. At this point the reaction mixture was cooled and the pH adjusted to approximately 8 using glacial acetic acid. This aqueous solution was then extracted with methylene chloride (3×40 mL) and the combined organic extracts were dried (MgSO$_4$) and concentrated in vacuo to give a clear oil which crystallized on standing. Recrystallization from ethanol-water yielded a white solid, m.p. 87°–89° C.

Anal. Calcd. for C$_{14}$H$_{19}$H$_3$O$_4$: C, 57.32; H, 6.54; N, 14.33. Found: C, 57.66; H, 6.60; N, 14.19.

Spectroscopy (IR, NMR, and mass spectrum) were consistent with the assigned structure.

e. The triazolone ether intermediate (III, 2.5 g), 1-(3-chloropropyl)-4-(3-chlorophenyl)piperazine (II, 2.45 g), potassium carbonate (4.7 g), tetrabutylammoniumhydrogen sulfate (TBAHS, 0.18 g), and potassium iodide (0.02 g) were refluxed in 20 mL acetonitrile for 18 hours. The reaction mixture was then filtered and the filtrate concentrated in vacuo to a residue which was heated in 10 mL of 6N HCl at 60° for 15 minutes. This acidic mixture was then chilled to 0° and made basic by the dropwise addition of 50% sodium hydroxide solution. This basic mixture (pH ca. 10) was extracted with methylene chloride (4×25 mL), dried (K$_2$CO$_3$) and concentrated in vacuo. Flash chromatography (4% methanol/methylene chloride) afforded 2.95 g (71%) of a viscous oil. The oil (Ia) was shown by spectroscopy (IR, NMR, mass spectrum) to be consistent with the assigned structure.

The base form of Ia can be converted to the hydrochloride salt by treatment of an ethanol solution of Ia with ethanolic HCl. The hydrochloride salt crystallizes on standing to produce white powder, m.p. 163° (dec).

Anal. Calcd. for C$_{25}$H$_{32}$ClN$_5$O$_3$.HCl.0.2 C$_2$H$_6$O: C, 57.57; H, 6.37; N, 13.40; Cl, 13.57. Found: C, 57.44; H, 6.38; N, 13.19; Cl, 13.35.

NMR (DMSO-d$_6$): 1.47 (3,d [6.1 Hz]); 2.18 (2,m); 3.18 (8,m); 3.77 (4,m); 4.18 (4,m); 4.81 (1,q [6.1 Hz]); 6.60 (1,bs); 6.95 (6,m); 7.27 (3,m); 11.50 (1,bs).

IR (KBr): 690, 760, 1105, 1245, 1445, 1490, 1600, 1700, 2500, 2930, and 3410 cm$^{-1}$.

EXAMPLE 2

General Preparation for Alkylation or Acylation of I (R=H)

A. Alkylation

The sodium salt of a Formula I compound wherein R=H is generated by reaction with sodium hydride in dimethylformamide, or another polar aprotic solvent, following which the salt is reacted with an alkyl iodide, or other appropriating alkylating agent (RX where X=Cl, Br, I, tosylate, etc.).

B. Acylation

Acylation can be achieved by direct condensation starting with a selected Formula I compound wherein R=H. In one method the Formula I alcohol compound is reacted with an appropriate acid chloride in the presence of a catalyst (e.g. 4-dimethylaminopyridine) in a suitable solvent such as methylene chloride. Alternatively, the Formula I alcohol compound can be reacted with an appropriate carboxylic acid in the presence of a condensing agent such as dicyclohexocarbodiimide.

Alkylation and acylation of secondary alcohols may be accomplished by a variety of synthetic methods which are well known to the chemical practitioner. By selection of the appropriate reagents and utilization of the above methodology, additional Formula I compounds may be prepared.

Additional Formula I Compounds

Z—(CH$_2$)$_n$—N (triazolone ring with OR group)—N—N (piperazine)—N—(3-chlorophenyl)

| Example No. | n | R | Z |
|---|---|---|---|
| 3 | 2 | —H | H |
| 4 | 3 | —CH(CH$_3$)$_2$ | PhO— |
| 5 | 2 | —CH$_2$CH$_2$CH$_2$CH$_3$ | 4-F—PhO— |
| 6 | 4 | —CH$_3$ | H |
| 7 | 2 | —C(O)CH$_3$ | PhO— |
| 8 | 3 | —C(O)—CH$_2$CH$_3$ | 4-MeO—PhO— |
| 9 | 4 | —CH$_2$CH$_2$—Ph | 3-CF$_3$—PhO— |
| 10 | 2 | —CH(CH$_3$)CH$_2$—Ph | H |
| 11 | 3 | —C(O)—Ph | 3-CF$_3$—PhO— |
| 12 | 2 | —C(O)—CH$_2$—Ph | 2-MeO—PhO— |
| 13 | 2 | —C(O)—CH$_2$CH$_2$CH$_2$—Ph | PhO— |
| 14 | 2 | H | 3-CF$_3$—PhO— |
| 15 | 3 | H | 3-CF$_3$—PhO— |
| 16 | 4 | H | PhO— |
| 17 | 3 | H | PhO— |
| 18 | 2 | H | 4-MeO—PhO— |

EXAMPLE 19

2-[3-[4-(3-Chlorophenyl)-1-piperazinyl]propyl]-2,4-dihydro-4-(2-phenoxyethyl)-5-[1-(phenylmethoxy)ethyl]-3(H)-1,2,4-triazol-3-one (I, R=benzyl; Z=OPh)

An alternate method for the preparation of ether compounds corresponding to Formula I (R=alkyl, phenylalkyl) follows. Sodium metal (about 12 g) was added cautiously to a stirred cold (ice bath) portion (250 mL) of benzyl alcohol. After most of the sodium metal had dissolved, the reaction was heated to 150° C. 2-Chloropropionic acid (27.2 g, 0.25 mole) was added dropwise in 35 mL of benzyl alcohol and the resulting mixture heated on additional 3 hours. Concentration in vacuo gave crude 2-benzyloxypropionic acid which was used without further purification.

About 44 g of the 2-benzyloxypropionic acid was dissolved in 200 mL methanol, cooled to 0°, and treated dropwise with thionyl chloride (29 g, 17.8 mL). Following completion of the addition, the reaction was maintained at 0° for an additional hour with rapid stirring and then placed in the refrigerator overnight. Distillation gave 40 g of the corresponding methyl ester, b.p. 64° at 0.1 Torr.

The ester was converted to the corresponding hydrazide by dropwise addition of the ester to a cold (0°) methanol solution containing anhydrous hydrazine. Distillation gave an 80% yield of hydrazide product, m.p. 120°–150° at 0.2 Torr.

This hydrazide intermediate product was utilized in the synthetic process depicted supra. as Scheme 1 and described in more detail in Example 1.

Finally, the triazolone ether intermediate (III, P=benzyl; Z=OPh; 1.5 g, 4.42 millimole), 1-(3-chloropropyl)-4-(3-chlorophenyl)piperazine (II, 1.27 g, 4.65 millimole), potassium carbonate (1.83 g, 13.27 millimole), and about 0.01 g amounts of potassium iodide and tetrabutylammonium hydrogen sulfate in acetonitrile (15 mL) was heated with stirring to reflux for 24 hours. The insolubles were removed by filtration and the filtrate was concentrated in vacuo to a yellow oil which was flashed chromatographed (4% methanol/methylene chloride) to yield 2.5 g (98%) of crude product as the base. The base was converted into the hydrochloride salt by treatment with ethereal HCl and ethanol thereby giving 1.8 g white solid, m.p. 163° (dec).

What is claimed is:

1. A compound in purified pharmaceutically acceptable form having formula I

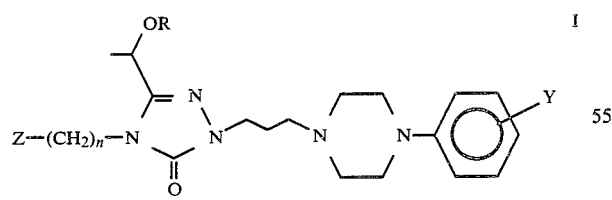

or a pharmaceutically acceptable salt thereof wherein
R is hydrogen, lower ($C_1$–$C_4$) alkyl, lower alkylcarbonyl, phenyl-lower alkyl, phenylcarbonyl, and phenyl-lower alkylcarbonyl;
n is 2–4;
Y is halogen and trifluoromethyl;
Z is hydrogen and

wherein $R^1$ is hydrogen, halogen, lower alkoxy and trifluoromethyl.

2. The compound of claim 1 in which R is hydrogen.
3. The compound of claim 1 in which Y is 3-chloro.
4. The compound of claim 1 in which R is benzyl.
5. The compound of claim 1 in which Z is phenyloxy.
6. The compound of claim 2 in which Y is 3-chloro.
7. The compound of claim 1, 2-[3-[4-(3-chlorophenyl)-1-piperazinyl]propyl]-5-(1-hydroxyethyl)-2,4-dihydro-4-(2-phenoxyethyl)-3H-1,2,4-triazol-3-one.
8. The pharmaceutically acceptable acid addition salt of 2-[3-[4-(3-chlorophenyl)-1-piperazinyl]propyl]-5-1-hydroxyethyl)-2,4-dihydro-4-(2-phenoxyethyl)-3H-1,2,4-triazol-3-one.
9. The antidepressant method which comprises administering to a mammalian host having depression a non-toxic antidepressant effective dose of a compound claimed in claim 1.
10. The antidepressant method of claim 9 wherein the compound administered is 2-[3-[4-(3-chlorophenyl)-1-piperazinyl]propyl]-5-(1-hydroxyethyl)-2,4-dihydro-4-(2-phenoxyethyl)-3H-1,2,4-triazol-3-one or a pharmaceutically acceptable salt thereof.
11. A pharmaceutical composition in dosage unit form suitable for systemic administration to a mammalian host comprising a pharmaceutical carrier and an amount of a Formula I compound, as claimed in claim 1, to provide an effective antidepressant but non-toxic dose.
12. A pharmaceutical composition of claim 11 wherein the formula I compound is 2-[3-[4-(3-chlorophenyl)-1-piperazinyl]propyl]-5-(1-hydroxyethyl)-2,4-dihydro-4-(2-phenoxyethyl)-3H-1,2,4-triazol-3-one or a pharmaceutically acceptable salt thereof.
13. The compound having Formula I

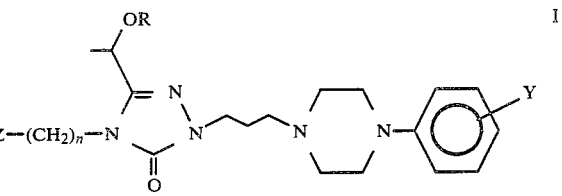

or a pharmaceutically acceptable salt thereof wherein
R is hydrogen, lower ($C_1$–$C_4$) alkyl, lower alkylcarbonyl, phenyl-lower alkyl, and phenyl-lower alkylcarbonyl;
n is 2–4;
Y is halogen and trifluoromethyl;
Z is hydrogen and

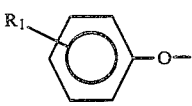

wherein $R^1$ is hydrogen, halogen, lower alkoxy and trifluoromethyl.

* * * * *